(12) United States Patent
Vogel et al.

(10) Patent No.: US 6,551,345 B2
(45) Date of Patent: Apr. 22, 2003

(54) PROTECTION APPARATUS FOR IMPLANTABLE MEDICAL DEVICE

(75) Inventors: Martin J. Vogel, Palmdale, CA (US); Richard J. Nelson, Canyon Country, CA (US); Robert A. Firth, Frazier Park, CA (US); Anthony D. Falco, Azusa, CA (US); Joseph H. Schulman, Santa Clarita, CA (US)

(73) Assignee: Alfred E. Mann Foundation for Scientific Research, Valencia, CA (US)

( * ) Notice: Subject to any disclaimer, the term of this patent is extended or adjusted under 35 U.S.C. 154(b) by 141 days.

(21) Appl. No.: 09/844,621

(22) Filed: Apr. 26, 2001

(65) Prior Publication Data

US 2002/0161402 A1 Oct. 31, 2002

(51) Int. Cl.⁷ .............................................. A61N 1/375
(52) U.S. Cl. ................................ 607/1; 607/27; 607/36
(58) Field of Search ................................ 206/438, 488, 206/570, 706–719, 722, 724; 257/257, 84, 79, 99, 355; 361/91.4, 91.5, 211–212, 220; 439/188, 510, 513; 607/1, 27, 29, 36, 37

(56) References Cited

U.S. PATENT DOCUMENTS

| 5,232,091 A | 8/1993 | Hennessy et al. |
|---|---|---|
| 5,514,892 A | 5/1996 | Countryman et al. |
| 5,562,489 A | 10/1996 | Cronin |
| 5,633,780 A | 5/1997 | Cronin |
| 5,637,901 A | 6/1997 | Beigel et al. |
| 5,697,501 A | 12/1997 | Johansen |
| 5,847,914 A | 12/1998 | Johansen et al. |
| 5,914,501 A | 6/1999 | Antle et al. |
| 6,052,623 A | * 4/2000 | Fenner et al. .................. 607/36 |
| 6,400,204 B1 | * 6/2002 | Davis .......................... 327/314 |
| 6,268,654 B1 | * 7/2002 | Glenn et al. ................. 257/704 |

* cited by examiner

*Primary Examiner*—Jeffrey R. Jastrzab
*Assistant Examiner*—Frances P. Oropeza
(74) *Attorney, Agent, or Firm*—Lee J. Mandell

(57) ABSTRACT

A method and apparatus for protecting an electronic implantable medical device prior to it being implanted in a patient's body. The apparatus affords protection against electronic component damage due to electrostatic discharge and/or physical damage due to improper handling. The apparatus is comprised of a circuit board having first and second spring clips mounted on the board. The spring clips are configured to receive and releasably grasp the electrodes of a medical device housing to support the housing just above the surface of the circuit board. First and second conductive paths are formed on the circuit board extending between the first and second clips for shunting electrostatic discharge currents to prevent such currents from passing through the device electronic circuitry. The respective shunt paths include oppositely oriented diodes, preferably comprising diodes which emit light (i.e., LEDs) when current passes therethrough.

23 Claims, 6 Drawing Sheets

US 6,551,345 B2

PROTECTION APPARATUS FOR IMPLANTABLE MEDICAL DEVICE

FIELD OF THE INVENTION

This invention relates generally to a method and apparatus for use with an electronic implantable medical device for protecting the device from physical and/or electrostatic discharge damage prior to medically implanting the device in a patient's body. Moreover, preferred embodiments of the invention afford the ability to functionally test the device without removing it from its shipping container prior to implantation.

BACKGROUND OF THE INVENTION

Many types of electronic medical devices are known which are intended for implantation in a patients body. Although these devices vary widely in design, they typically include a housing containing electronic circuitry connected to two or more electrodes which extend exteriorly from the housing (or one or more electrode when the housing is the other electrode). The circuitry can, for example, include a functional circuit (e.g., a pulse generator), a power supply circuit (e.g., rechargeable battery), and a transceiver for wirelessly communicating with an external controller. Implantable medical devices of this sort are useful in a variety of applications for stimulating muscle or nerve tissue and/or monitoring body parameters.

To minimize device failure and maximize device reliability, it is important that an electronic medical device be properly handled along the entire chain from manufacturing, through shipping and storage, and on to the medical procedure for implanting the device in a patient's body. For example, improper handling can subject the device to physical damage and/or component damage due to electrostatic discharge (ESD).

SUMMARY OF THE INVENTION

The present invention is directed to a method and apparatus for protecting an electronic implantable medical device prior to it being implanted in a patient's body. More particularly, a method and apparatus in accordance with the invention affords protection to the medical device from just after manufacture to just prior to implantation. Protection is afforded against electronic component damage due to electrostatic discharge and/or physical damage due to improper handling.

Embodiments of the invention are particularly valuable when used with small fragile medical devices which often comprise an electronic circuit housing having a diameter of less than 6 mm and an axial length of less than 60 mm. The housing typically contains electronic circuitry which is electrically connected to first and second electrodes which extend exteriorly from the housing.

A preferred apparatus in accordance with the invention is comprised of a circuit board having first and second spring clips mounted on the board.

The spring clips are configured to receive and releasably grasp the electrodes of a medical device housing to support the housing just above the surface of the circuit board. First and second conductive paths are formed on the circuit board extending between the first and second clips for shunting electrostatic discharge currents to prevent such currents from passing through the device electronic circuitry. Preferably, the respective shunt paths include oppositely oriented diodes, preferably comprising diodes which emit light (i.e., LEDs) when current passes therethrough.

In accordance with the invention, a medical device is preferably mounted in the protective apparatus as a late step in the device manufacturing process. The protection apparatus/device combination is then placed into a shipping container. The combination remains engaged until the device is ready for medical implantation in a patient's body. The shipping container preferably includes a transparent window through which the light emitting diodes are visible.

In a preferred method in accordance with the invention, the medical device is sterilized, e.g., using steam or ethylene oxide (ETO), after being placed in the shipping container.

A significant feature of the invention allows the medical device to be functionally tested while in the shipping container. More particularly, exemplary medical devices include (1) transceivers which permit wireless communication of commands and data between an external controller and the device electronic circuitry and (2) battery charging circuits which extract energy from an external power source, e.g., via an alternating magnetic field, for charging a device battery. In accordance with the invention, a medical device can be functionally tested while still in the shipping container by transmitting a command or activation signal to the device. If the device is functioning properly, it will respond in a particular manner, as by outputting a sequence of pulses whose characteristics (e.g., frequency, pulse width, etc.) indicate proper operability. This output pulse sequence drives the protection apparatus LEDs which can be monitored to detect whether the device is operating within specifications. Additionally, the device battery can be charged while still in the shipping container by an external power source.

DETAILED DESCRIPTION OF THE PREFERRED EMBODIMENTS

Figure 1:
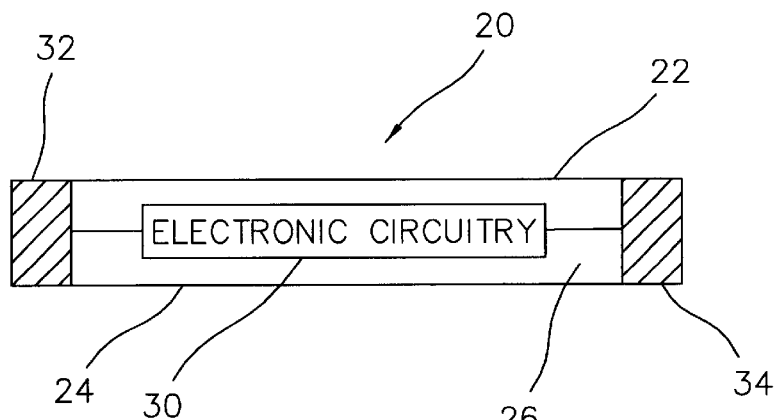
FIG. 1 schematically depicts the structure of an exemplary electronic implantable medical device of the type intended for use with the present invention.

Attention is initially directed to FIG. 1 which schematically depicts an electronic implantable medical device 20.

The device 20 is intended to be representative of a wide range of known electronic devices designed to be medically implanted in a patient's body for a variety of applications. For example only, such devices can be controlled to selectively stimulate muscle and nerve tissue and/or monitor and report various body parameters. The exemplary device 20 is depicted as comprising an elongate housing 22 defined by a peripheral wall 24 enclosing an interior volume 26. The housing 22 can be variously shaped but, for simplicity herein, it will be assumed to be cylindrical. Typically such implantable medical devices are small in size, e.g., preferably less than 60 mm in length and less than 6 mm in diameter, and relatively fragile structurally. Reasonable care must be exercised in handling the devices 20 to prevent physical damage.

The exemplary device 20 is depicted as containing electronic circuitry 30 within the interior volume 26. The circuitry 30 is connected between first and second electrodes 32, 34 which extend exteriorly from the housing 22. The circuitry 30 typically includes sensitive electronic components which can be permanently damaged by high currents which can be caused, for example, by electrostatic discharge (ESD). Accordingly, as with many other electronic devices, it is advisable to exercise appropriate care to avoid discharging high currents through the circuitry 30. The present invention is primarily directed to a method and apparatus as depicted in FIGS. 3–8, for protecting the device 20, from damage while being shipped, stored, and handled between a late manufacturing stage and up to the time it is implanted in a patient's body.

Figure 2:
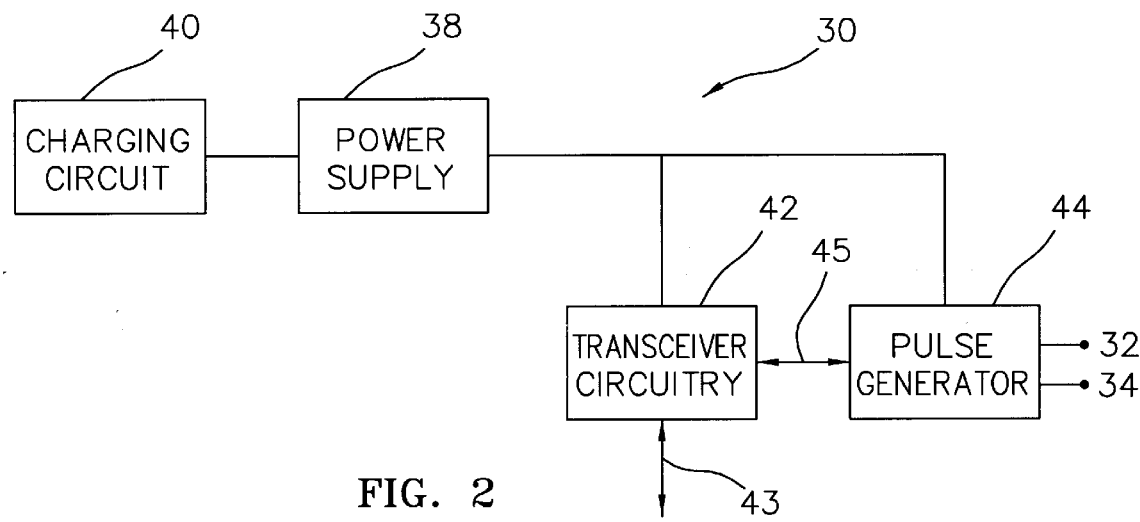
FIG. 2 is a block diagram generally representing the electronic circuitry typically employed in the exemplary medical device of FIG. 1.

FIG. 2 is a block diagram which generally depicts the functional components of typical electronic circuitry 30 employed in implantable medical devices 20. More particularly, the electronic circuitry 30 is shown as comprising a power supply 38 which may include a rechargeable battery or a capacitor (not shown). A charging circuit 40 is connected to the power supply 38 for deriving energy from an external power source to charge the battery. For example only, the charging circuit can respond to an alternating, e.g., amplitude modulated or frequency modulated, magnetic field or RE field to supply a charging current to the power supply 38. The power supply 38 is depicted as supplying operating voltage to a transceiver circuitry 42 and a pulse generator 44. The transceiver circuitry 42 is configured to communicate with an external controller (not shown) employing a suitable form of wireless communication via path 43, typically radio communication. Commands and data can be supplied via path 43 from the external controller to the transceiver circuitry 42 for controlling or programming the pulse generator 44. The pulse generator 44 can in turn provide data to the transceiver circuit 42 via path 45 for communication to the external controller.

It should be understood that FIG. 2 is intended to only very generally depict the functionality of the electronic circuitry 30 contained in the device 20. The method and apparatus of the invention to be described herein, is useful in combination with a wide variety of medical devices 20, e.g., muscle stimulators, neural stimulators, physiological sensors, pacemakers, etc.

Figure 3:
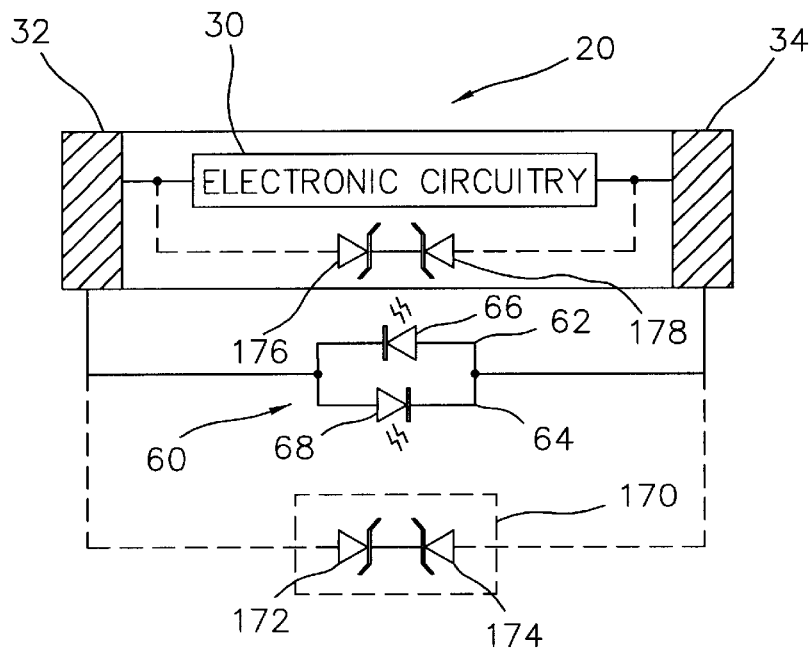
FIG. 3 schematically depicts the exemplary medical device of FIG. 1 used in combination with a protection apparatus in accordance with the present invention.

Attention is now directed to FIG. 3 which depicts an electronic protection circuit 60 externally connected between the device electrodes 32, 34. The protection circuit 60 is comprised of first and second shunt paths 62, 64 which each include a unidirectional current device, e.g., a diode. Shunt path 62 contains diode 66 oriented from electrode 32 to electrode 34. Shunt path 64 contains diode 68 which is oppositely oriented, i.e., from electrode 34 to electrode 32.

The shunt paths 62 and 64 operate to shunt current spikes which can be caused, for example, by electrostatic discharge around electronic circuitry 30.

As will be discussed hereinafter, the diodes 66, 68 preferably have an audible or light generator associated therewith to indicate current therethrough. More specifically, preferred embodiments of the invention are preferably implemented with light emitting diodes (LEDs). As will be understood hereinafter, it is preferable for the respective LEDs to produce light of different colors so that the direction of current flow between electrodes 32 and 34 can be readily determined by an observer.

Figure 4:
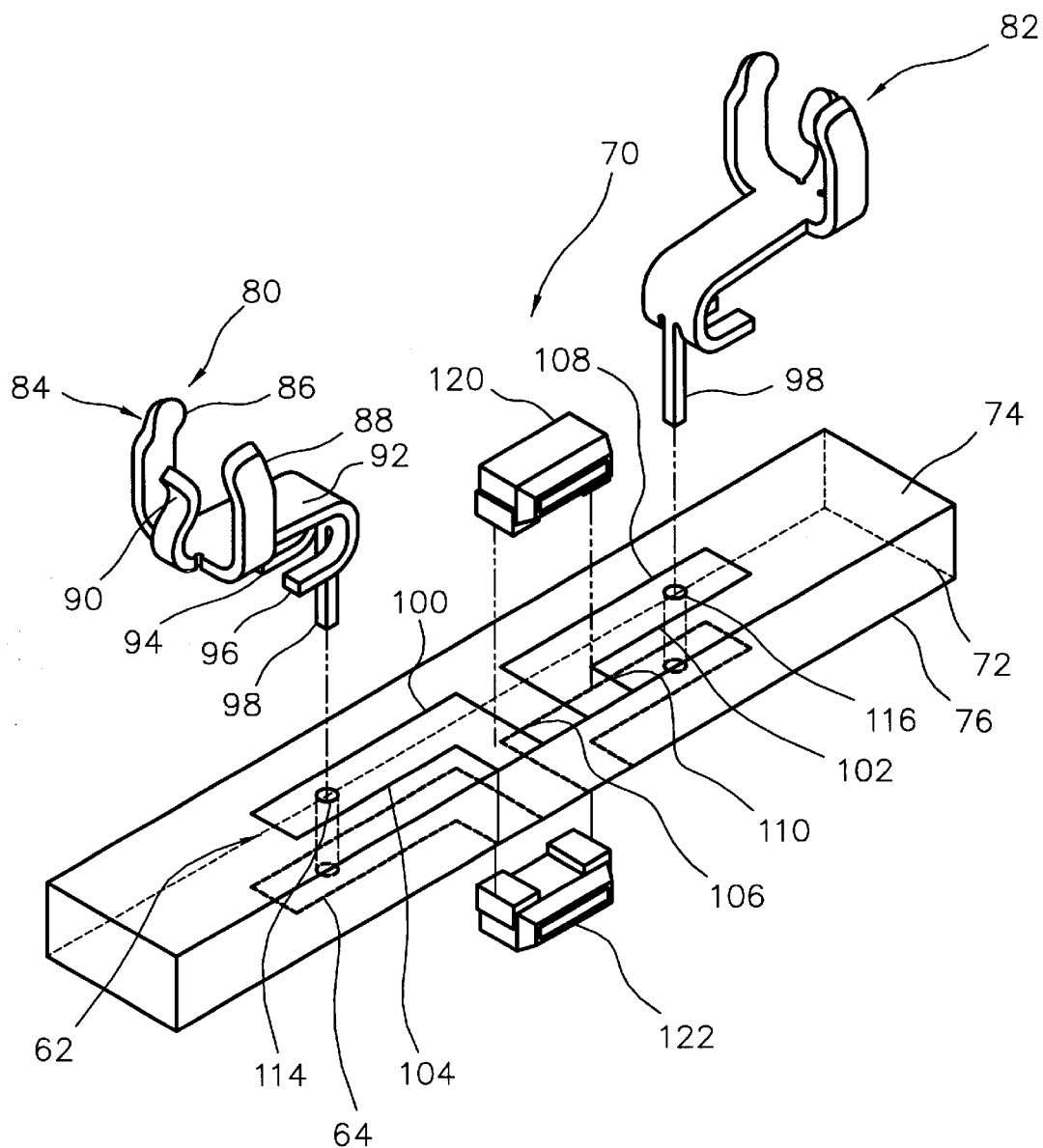
FIG. 4 is an exploded isometric illustration depicting a protection apparatus in accordance with the present invention.

FIG. 4 depicts a preferred implementation of a protection apparatus 70 in accordance with the present invention tailored for use with the exemplary cylindrical medical device 20. The apparatus 70 is comprised of a substrate or circuit board 72 having an upper surface 74 and a lower surface 76.

First and second spring contact clips 80, 82 are provided for mounting on the circuit board 72. Each clip is essentially comprised of a cradle portion 84 including spaced first and second resilient arms 86, 88. The arms 86, 88, together with end finger 90, define a cradle for releasably retaining an electrode 32, 34 of device 20. The cradle portion 84 is cantilevered by a shank portion 92 which extends to spaced contact fingers 94, 96 and to a post 98. The clips 80,82 can be inexpensively formed by a stamping and bending operation.

First and second spring contact clips 80, 82 are provided for mounting on the circuit board 72. Each clip is essentially comprised of a cradle portion 84 including spaced first and second resilient arms 86, 88. The arms 86, 88, together with end finger 90, define a cradle for releasably retaining an electrode 32, 34 of device 20. The cradle portion 84 is cantilevered by a shank portion 92 which extends to spaced contact fingers 94, 96 and to a post 98. The clips 80, 82 can be inexpensively formed by a stamping and bending operation.

Figure 5:
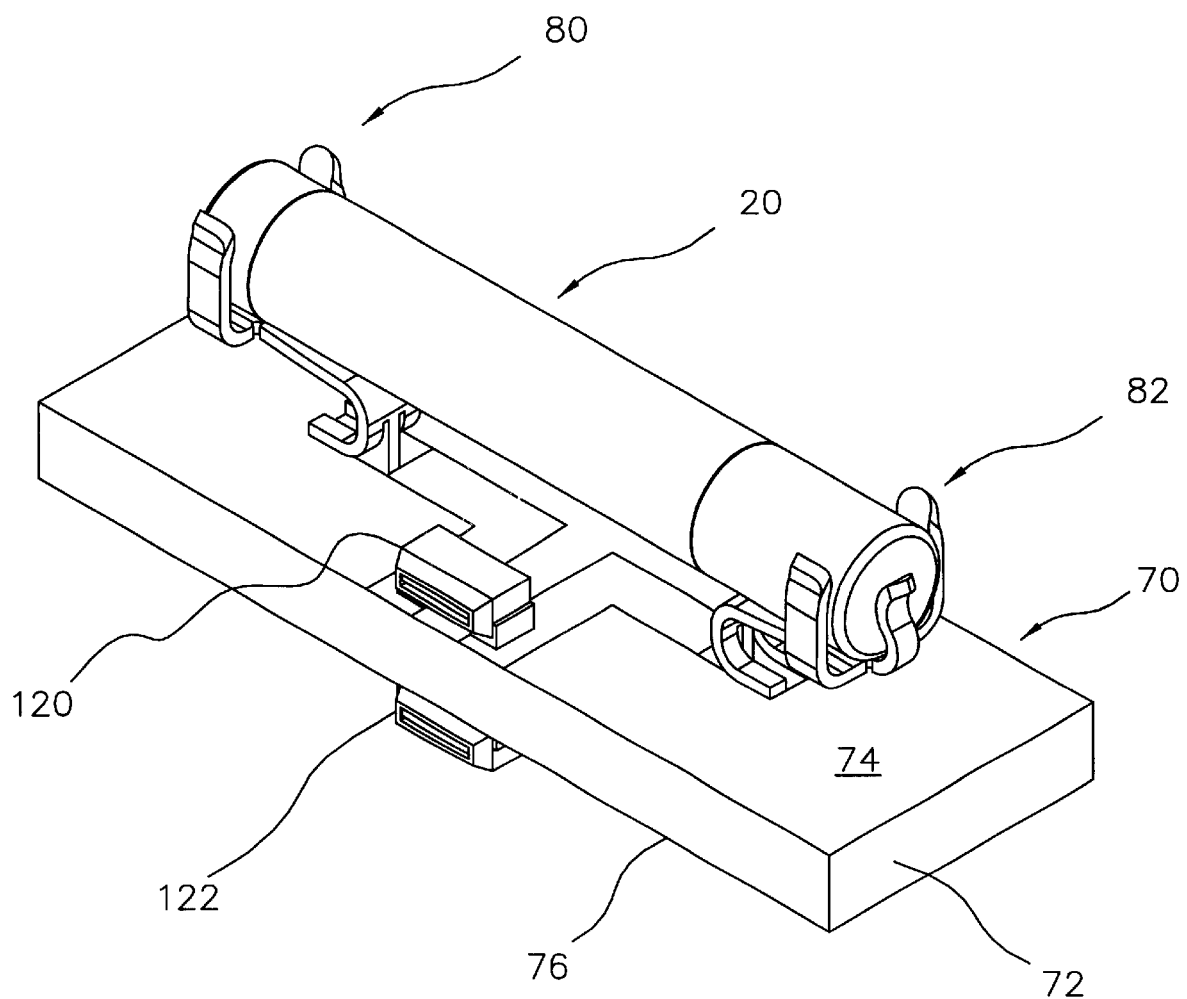
FIG. 5 is an exploded isometric illustration depicting a protection apparatus in accordance with the present invention for accommodating a medical device to be protected.
Figure 6:
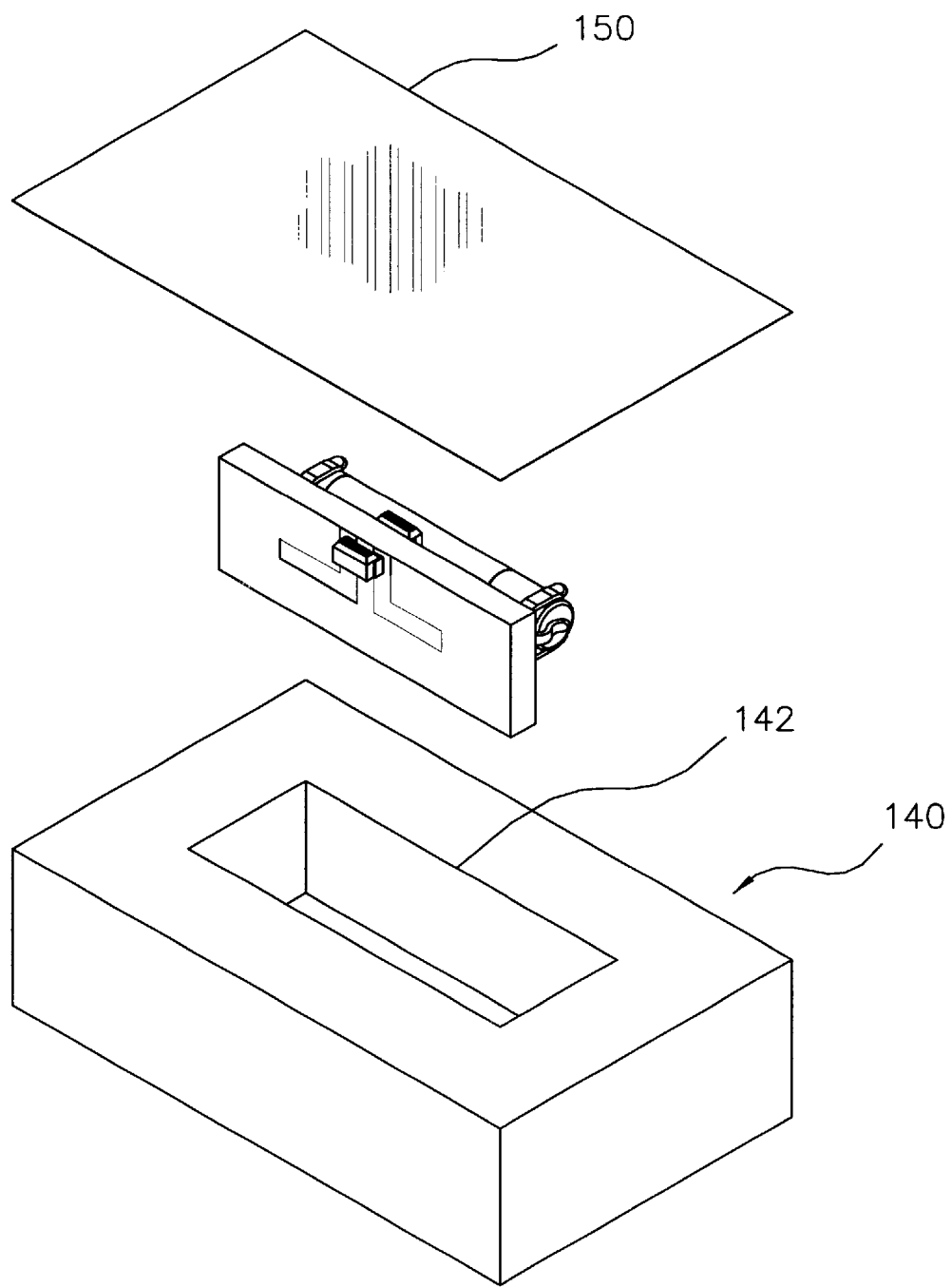
FIG. 6 is an exploded isometric illustration depicting the manner of placing the protection apparatus and medical device into a shipping container.
Figure 7:
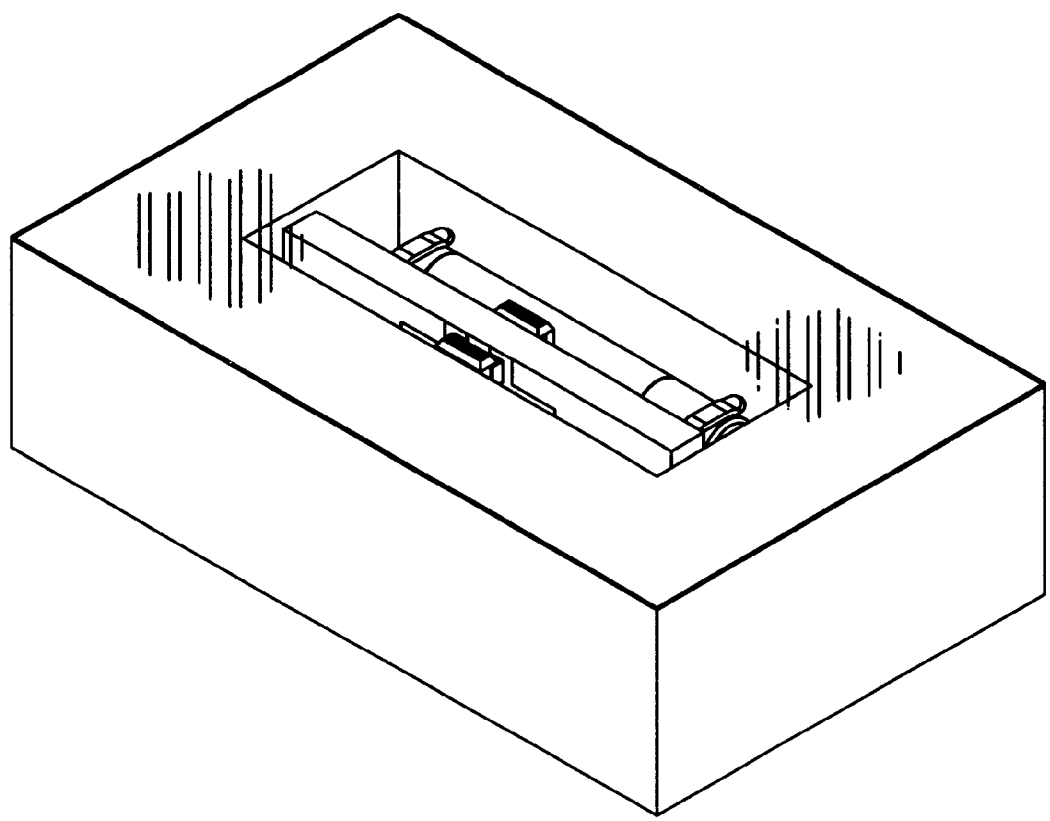
FIG. 7 is an isometric view depicting the protection apparatus and medical device received in the shipping container and oriented so that the light emitting diodes (LEDs) of the apparatus are visible through a container transparent window.

FIG. 5 shows the medical device 20 accommodated in the clips 80 and 82 and with the LEDs 120, 122 being mounted on opposite surfaces 74 and 76 of circuit board 72. In accordance with the invention, the device 20 is mounted into the clips 80, 82 in a late stage of the manufacturing process of device 20. Thereafter, the mated protection apparatus 70 and medical device 20 are placed in a shipping container 140, as depicted in FIG. 6. Shipping container 140 can be inexpensively formed of molded plastic, and preferably includes a cavity 142 shaped and dimensioned to accommodate the mated protection apparatus 70 and medical device 20. In placing the mated combination in the cavity, circuit board 72 should be oriented so that the LEDs 120 and 122 face upwardly. A transparent sheet 150 covers the cavity 142, to define a window through which the LEDs 120 and 122 are visible as depicted in FIG. 7.

It is intended that the protection apparatus 70 and medical device 20 remain mated together in the shipping container 140 for the full duration of its shelf life from the manufacturing stage to just prior to medically implanting the device 20 in a user's body. After the mated protection apparatus and medical device 20 are placed into the shipping container 140 and the cavity 142 sealed by transparent sheet 150, the device 20 is preferably sterilized using a known gas, e.g., ethylene oxide (ETO), or steam process. For its entire life between manufacturing and implantation, the protection apparatus 70 will protect the medical device from electronic component damage attributable to electrostatic discharge (ESD). Moreover, the apparatus 70 protects device 20 against physical damage because it is firmly retained by spring clips 80, 82 mounted on the substantially rigid circuit board 72.

Figure 8:
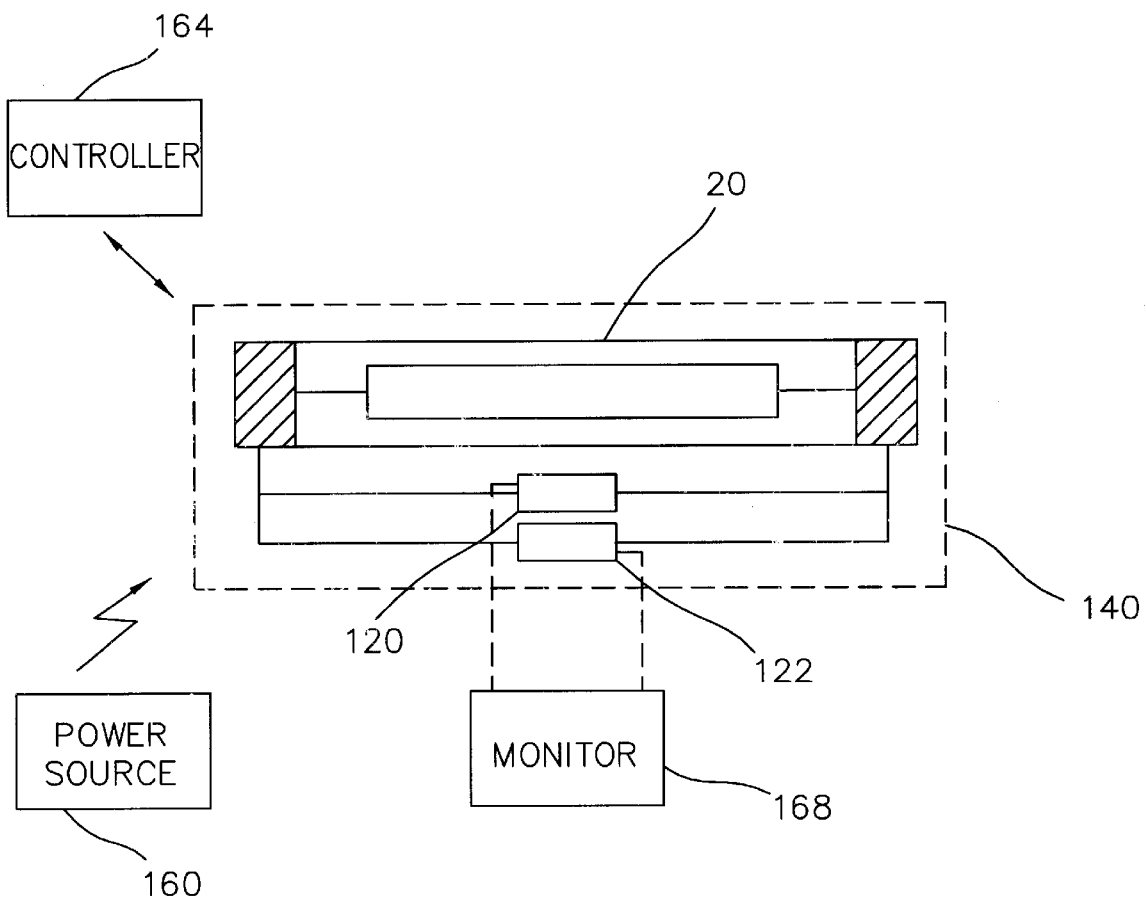
FIG. 8 is a block schematic diagram depicting how the medical device is tested while in the shipping container.

In accordance with the present invention, the device 20 is preferably functionally tested while still in its shipping container 140. More particularly, as depicted in FIG. 8, an external power source 160 is able to charge the on-board device battery via the aforementioned charging circuit 40 by generating an appropriate field, e.g., alternating magnetic field, in close proximity to the device 20. The power source 160 can be similar or identical to the power source normally used to charge the battery after the device is implanted in a user's body. Similarly, an external controller 164 can be used to provide commands and receive data from the medical device 20 while it is still contained within the shipping container 140. In a particularly useful procedure, the controller 164 is able to wirelessly communicate a command or activation signal to the device 20, e.g., via an RF signal. The controller 164 can be similar or identical to a controller used by the user or by a physician to program the device 20 after implantation in the user's body. The procedure depicted in FIG. 8 contemplates that the controller 164 provide an activation signal to the medical device 20 while it is still in the shipping container 140. The electronic circuitry of the device 20 is designed to respond to the activation signal to cause pulse generator 44 to output a known pulse sequence between electrodes 32 and 34. This pulse sequence will cause LEDs 120 and 122 to illuminate in accordance with a pattern having known characteristics (e.g., frequency, pulse width, etc.). The activity of the LEDs 120 and 122 can be monitored by monitor 168 to determine whether the device 20 is operating properly. For example, if the device 20 is configured to generate monophasic pulses, one LED will "brightly" light during generation of each pulse and the other LED will "dimly" light during recharge of the pulse generator 44. Alternatively, if the device 20 is configured to generate a biphasic pulse, the intensity of the light emitted from each LED will be approximately the same.

Thus, it will be appreciated that the protection apparatus 70 in accordance with the present invention offers both electrical and physical protection of the device 20 during shipping and handling, and facilitates the testing of the device prior to its being medically implanted in a user's body.

Thus, it will be appreciated that the protection apparatus 70 in accordance with the present invention offers both electrical and physical protection of the device 20 during shipping and handling, and facilitates the testing of the device prior to it being medically implanted in a user's body.

Although a specific embodiment of the invention has been described, it is recognized that variations and modifications will readily occur to those skilled in the art coming within the intended spirit and scope of the present invention as defined by the appended claims. For example, as previously described and shown in FIG. 3, LEDs 66, 68 serve a diagnostic and ESD protection function. However, in some environments it may be desirable to further enhance the ESD protection already provided by the LEDs 66, 68 by additionally supplying an internal ESD protection network. For example, see FIG. 2 where zener diodes 176 and 178 are placed in series across the electronic circuitry 30 within the housing 22. In such a case, the zener voltage is selected to be larger than the largest pulse that can be produced by the electronic circuitry 30. Alternatively, apparatus 70 may additionally include an ESD protection network 170, e.g., comprised of a pair of reversed zener diodes 172, 174 connected in series (with the zener voltage small enough to suppress ESD but large enough to enable the LEDs to illuminate) or a transient voltage suppression (TVS) device, in parallel with the LEDs (see, for example, DZ000110A manufactured by Micro Semi Corporation of Scottsdale, Ariz., USA). Furthermore, while the aforedescribed apparatus 70 shown in FIG. 4 is particularly suited for use with the exemplary small, cylindrical device of FIG. 1, the present invention includes the use of the aforedescribed protection circuitry with other differently shaped medical devices having two or more electrodes. In such cases, the mounting brackets would be adjusted accordingly to accommodate the particular device.

What is claimed is:

1. An apparatus for physically and electrically protecting an electronic medical device having first and second electrodes prior to it being implanted in a patient's body, said apparatus comprising:

first and second contact clips for electrically respectively contacting the first and second electrodes on the medical device;

first and second circuit paths connected between said first and second contact clips, said first and second circuit paths respectively including oppositely oriented first and second unidirectional current devices to thereby serve to protect the medical device from electrostatic discharge prior to implantation; and wherein said apparatus is configured to be separated from the medical device before implantation.

2. The apparatus of claim 1 further including:

a circuit board;

said contact clips being mounted on said circuit board for contacting the electrodes and supporting the medical device; and wherein said first and second circuit paths are formed on said circuit board.

3. An apparatus for physically and electrically protecting an electronic medical device having first and second electrodes prior to it being implanted in a patient's body, said apparatus comprising:

first and second contact clips for electrically respectively contacting the first and second electrodes on the medical device;

first and second circuit paths connected between said first and second contact clips, said first and second circuit paths respectively including oppositely oriented first and second unidirectional current devices; and wherein said first and second unidirectional current devices comprise light emitting diodes.

4. An apparatus for physically and electrically protecting an electronic medical device having first and second electrodes prior to it being implanted in a patient's body, said apparatus comprising:

first and second contact clips for electrically respectively contacting the first and second electrodes on the medical device;

first and second circuit paths connected between said first and second contact clips, said first and second circuit paths respectively including oppositely oriented first and second unidirectional current devices;

a protection network electrically connected across said first and second contact clips to suppress electrostatic discharge; and wherein said protection network comprises a pair of unidirectional current devices serially connected in opposing polarities.

5. An apparatus for use with an implantable housing carrying first and second externally accessible electrodes and internally containing electronic circuitry connected to the first and second electrodes, said apparatus comprising:
- a substrate;
- a first spring clip mounted on said substrate, said first spring clip configured to electrically contact and releasably retain the first electrode;
- a second spring clip mounted on said substrate, said spring contact clip configured to electrically contact and releasably retain the second electrode;
- first and second shunt paths carried by said substrate connected between said first and second spring clips, said first and second shunt paths respectively including oppositely oriented unidirectional current devices to thereby serve to protect the electronic circuitry within said implantable housing from electrostatic discharge prior to implantation; and wherein
    - said apparatus is configured to be separated from the implantable housing before implantation.

6. The apparatus of claim 5 wherein said substrate comprises a substantially rigid circuit board.

7. An apparatus for use with an implantable housing carrying first and second externally accessible electrodes and internally containing electronic circuitry connected to the first and second electrodes, said apparatus comprising:
- a substrate;
- a first spring clip mounted on said substrate, said first spring clip configured to electrically contact and releasably retain the first electrode;
- a second spring clip mounted on said substrate, said spring contact clip configured to electrically contact and releasably retain the second electrode;
- first and second shunt paths carried by said substrate connected between said first and second spring clips, said first and second shunt paths respectively including oppositely oriented unidirectional current devices; and wherein
    - said first and second shunt paths respectively include first and second light emitting diodes.

8. An apparatus for use with an implantable housing carrying first and second externally accessible electrodes and internally containing electronic circuitry connected to the first and second electrodes, said apparatus comprising:
- a substrate;
- a first spring clip mounted on said substrate, said first spring clip configured to electrically contact and releasably retain the first electrode;
- a second spring clip mounted on said substrate, said spring contact clip configured to electrically contact and releasably retain the second electrode;
- first and second shunt paths carried by said substrate connected between said first and second spring clips, said first and second shunt paths respectively including oppositely oriented unidirectional current devices;
- a protection network electrically connected across said first and second spring clips to suppress electrostatic discharge; and wherein
    - said protection network comprises a pair of unidirectional current devices serially connected in opposing polarities.

9. In combination with a medical device configured to be implanted in a patient's body, the device including a housing containing electronic circuitry connected to first and second electrodes extending exteriorly from the housing, an apparatus for use with the medical device prior to it being implanted, said apparatus comprising:
- a dielectric substrate carrying spaced first and second conductive contact clips, each of said clips being configured to electrically contact and physically retain one of the electrodes;
- a first shunt circuit carried by said substrate electrically connected between said first and second contact clips;
- a second shunt circuit carried by said substrate electrically connected between said first and second contact clips; wherein
    - said first and second shunt circuits respectively include oppositely directed first and second diodes to thereby serve to protect the medical device from electrostatic discharge prior to implantation to thereby serve to protect the medical device from electrostatic discharge prior to implantation; and wherein
    - said apparatus is configured to be separated from the medical device before implantation.

10. In combination with a medical device configured to be implanted in a patient's body, the device including a housing containing electronic circuitry connected to first and second electrodes extending exteriorly from the housing, an apparatus for use with the medical device prior to it being implanted, said apparatus comprising:
- a dielectric substrate carrying spaced first and second conductive contact clips, each of said clips being configured to electrically contact and physically retain one of the electrodes;
- a first shunt circuit carried by said substrate electrically connected between said first and second contact clips;
- a second shunt circuit carried by said substrate electrically connected between said first and second contact clips; and wherein
    - said first and second shunt circuits respectively include oppositely directed first and second diodes to thereby serve to protect the medical device from electrostatic discharge prior to implantation, wherein said first and second diodes each include means for emitting light in response to current therethrough.

11. The combination of claim 10 further including a monitor for sensing the response of said diodes to an externally provided activation signal supplied to said electronic circuitry.

12. The combination of claim 1 wherein said externally provided activation signal is wirelessly supplied to said electronic circuitry.

13. In combination with a medical device configured to be implanted in a patient's body, the device including a housing containing electronic circuitry connected to first and second electrodes extending exteriorly from the housing, an apparatus for use with the medical device prior to it being implanted, said apparatus comprising:
- a dielectric substrate carrying spaced first and second conductive contact clips, each of said clips being configured to electrically contact and physically retain one of the electrodes;
- a first shunt circuit carried by said substrate electrically connected between said first and second contact clips;
- a second shunt circuit carried by said substrate electrically connected between said first and second contact clips; wherein
    - said first and second shunt circuits respectively include oppositely directed first and second diodes to thereby serve to protect the medical device from electrostatic discharge prior to implantation;

a shipping container defining a transparent window; and wherein
said apparatus is accommodated in said shipping container with said diodes visible through said window.

14. In combination with a medical device configured to be implanted in a patient's body, the device including a housing containing electronic circuitry connected to first and second electrodes extending exteriorly from the housing, an apparatus for use with the medical device prior to it being implanted, said apparatus comprising:

a dielectric substrate carrying spaced first and second conductive contact clips, each of said clips being configured to electrically contact and physically retain one of the electrodes;

a first shunt circuit carried by said substrate electrically connected between said first and second contact clips;

a second shunt circuit carried by said substrate electrically connected between said first and second contact clips; wherein said first and second shunt circuits respectively include oppositely directed first and second diodes to thereby serve to protect the medical device from electrostatic discharge prior to implantation;

a protection network electrically connected across said first and second contact clips to suppress electrostatic discharge; and wherein said protection network comprises a pair of unidirectional current devices serially connected in opposing polarities.

15. A method of protecting an implantable medical device prior to implantation, the device comprising a housing containing electronic circuitry connected between first and second electrodes extending exteriorly from the housing, said method comprising:

providing first and second contacts for electrically contacting the first and second electrodes;

providing a first shunt path between said first and second contacts including a first current device oriented to permit current therethrough only from said first to said second contact; and providing a second shunt path between said first and second contacts including a second current device oriented to permit current therethrough only from said second to said first contact, whereby said first and second shunt paths serve to protect the medical device from electrostatic discharge prior to implantation to thereby serve to protect the medical device from electrostatic discharge prior to implantation; and wherein said apparatus is configured to be separated from the medical device before implantation.

16. The method of claim 15 further including:

providing a substantially rigid substrate for supporting said first and second contacts, said first shunt path, and said second shunt path; and configuring first and second contacts for releasably grasping electrodes and physically retaining the housing relative to said substrate.

17. A method of protecting an implantable medical device prior to implantation, the device comprising a housing containing electronic circuitry connected between first and second electrodes extending exteriorly from the housing, said method comprising:

providing first and second contacts for electrically contacting the first and second electrodes;

providing a first shunt path between said first and second contacts including a first current device oriented to permit current therethrough only from said first to said second contact;

providing a second shunt path between said first and second contacts including a second current device oriented to permit current therethrough only from said second to said first contact; and providing an indicator in at least one of said shunt paths to indicate current therethrough.

18. A method of protecting an implantable medical device prior to implantation, the device comprising a housing containing electronic circuitry connected between first and second electrodes extending exteriorly from the housing, said method comprising:

providing first and second contacts for electrically contacting the first and second electrodes;

providing a first shunt path between said first and second contacts including a first current device oriented to permit current therethrough only from said first to said second contact;

providing a second shunt path between said first and second contacts including a second current device oriented to permit current therethrough only from said second to said first contact;

emitting light in said first shunt path to indicate current therethrough; and emitting light in said second shunt path to indicate current therethrough.

19. The method of claim 18 further including:

providing a shipping container defining a transparent window; and placing said device in said shipping container oriented so that light emissions from said first and second shunt paths are visible through said window.

20. The method of claim 19 further including sterilizing the device while in said shipping container.

21. The method of claim 19 further including:

applying an activation signal to the device while in said shipping container; and monitoring the light emissions from said shunt paths in response to the application of said activation signal.

22. The method of claim 21 wherein said step of applying an activation signal comprises providing wireless communicating energy to the electronic circuitry in the housing.

23. A method of protecting an implantable medical device prior to implantation, the device comprising a housing containing electronic circuitry connected between first and second electrodes extending exteriorly from the housing, said method comprising:

providing first and second contacts for electrically contacting the first and second electrodes;

providing a first shunt path between said first and second contacts including a first current device oriented to permit current therethrough only from said first to said second contact;

providing a second shunt path between said first and second contacts including a second current device oriented to permit current therethrough only from said second to said first contact;

providing a protection network electrically connected across said first and second contacts to suppress electrostatic discharge; and wherein said protection network comprises a pair of unidirectional current devices serially connected in opposing polarities.

* * * * *

UNITED STATES PATENT AND TRADEMARK OFFICE
CERTIFICATE OF CORRECTION

PATENT NO. : 6,551,345 B2
DATED : April 22, 2003
INVENTOR(S) : Vogel et al.

Page 1 of 1

It is certified that error appears in the above-identified patent and that said Letters Patent is hereby corrected as shown below:

Column 5,
Line 43, should read as follows:
-- device prior to it being medically implanted in a user's --
Lines 45-49, delete.
Line 45, insert -- It is important that medical devices intended for implantation in a patient's body be biocompatible, i.e., that they employ materials which do not produce deleterious effects on the living tissue. This requirement dictates a choice of appropriate biocompatible materials. In order to avoid compromising biocompatibility, it is preferable that the contact clips 80, 82 which physically contact the electrodes 32, 34 of the device 20 also be formed of an appropriate biocompatible material, e.g., platinum. --

Column 8,
Line 46, should read as follows:
12. The combination of claim 11 wherein said externally Signed and Sealed this Third Day of August, 2004

JON W. DUDAS
*Acting Director of the United States Patent and Trademark Office*